United States Patent
O'Neil et al.

(10) Patent No.: US 9,282,979 B2
(45) Date of Patent: Mar. 15, 2016

(54) INSTRUMENTS AND METHODS FOR NON-PARALLEL DISC SPACE PREPARATION

(75) Inventors: Michael J. O'Neil, Raynham, MA (US); Douglas Raymond, Raynham, MA (US); Jonathan Bellas, Raynham, MA (US); Derek Shaw, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1077 days.

(21) Appl. No.: 13/163,471

(22) Filed: Jun. 17, 2011

(65) Prior Publication Data

US 2011/0319898 A1    Dec. 29, 2011

Related U.S. Application Data

(60) Provisional application No. 61/358,220, filed on Jun. 24, 2010, provisional application No. 61/379,194, filed on Sep. 1, 2010, provisional application No. 61/385,958, filed on Sep. 23, 2010, provisional application No. 61/410,177, filed on Nov. 4, 2010, provisional application No. 61/397,716, filed on Nov. 30, 2010, provisional application No. 61/466,302, filed on Mar. 22, 2011.

(51) Int. Cl.

| | |
|---|---|
| *A61B 17/16* | (2006.01) |
| *A61M 29/00* | (2006.01) |
| *A61B 17/56* | (2006.01) |
| *A61B 17/17* | (2006.01) |
| *A61M 29/02* | (2006.01) |
| *A61F 2/44* | (2006.01) |
| *A61F 2/46* | (2006.01) |
| *A61B 5/00* | (2006.01) |

(Continued)

(52) U.S. Cl.
CPC ......... *A61B 17/1671* (2013.01); *A61B 17/1659* (2013.01); *A61B 17/1757* (2013.01); *A61F 2/447* (2013.01); *A61F 2/4611* (2013.01); *A61M 29/02* (2013.01); *A61B 5/4893* (2013.01); *A61B 2017/0256* (2013.01); *A61B 2017/3433* (2013.01); *A61M 25/0054* (2013.01); *A61M 25/0133* (2013.01)

(58) Field of Classification Search
CPC .................. A61B 17/1631; A61B 2017/1602; A61B 17/1671; A61B 17/1633
USPC .............................. 606/84, 85, 86 R, 279, 79
See application file for complete search history.

(56) References Cited

U.S. PATENT DOCUMENTS

| 4,105,034 A | 8/1978 | Shalaby |
| 4,130,639 A | 12/1978 | Shalaby |

(Continued)

FOREIGN PATENT DOCUMENTS

| DE | 10357960 | 7/2005 |
| EP | 609084 | 9/1997 |

(Continued)

OTHER PUBLICATIONS

U.S. Pat. No. 5,545,827, 10/1995, Aust (withdrawn).

(Continued)

*Primary Examiner* — Christian Sevilla
(74) *Attorney, Agent, or Firm* — Raymond N. Scott, Jr.

(57) ABSTRACT

Flexible shavers and curved access ports that reduce access and trajectory problems associated with conventional lateral approaches to the lower spine. These devices and methods allow for preparing a disc space in the lower spine at an angle that is parallel to the disc space. Consequently, these devices and methods allow for preparing with less endplate damage.

22 Claims, 13 Drawing Sheets

(51) Int. Cl.
   *A61B 17/02* (2006.01)
   *A61B 17/34* (2006.01)
   *A61M 25/00* (2006.01)
   *A61M 25/01* (2006.01)

(56) References Cited

U.S. PATENT DOCUMENTS

| | | |
|---|---|---|
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,538,612 A | 9/1985 | Patrick, Jr. |
| 4,834,757 A | 5/1989 | Brantigan |
| 5,006,121 A | 4/1991 | Hafeli |
| 5,019,082 A | 5/1991 | Frey |
| 5,133,719 A | 7/1992 | Winston |
| 5,163,939 A | 11/1992 | Winston |
| 5,169,402 A | 12/1992 | Elloy |
| 5,171,278 A | 12/1992 | Pisharodi |
| 5,217,475 A | 6/1993 | Kuber |
| 5,250,061 A | 10/1993 | Michelson |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,454,815 A | 10/1995 | Geisser |
| 5,454,827 A | 10/1995 | Aust |
| 5,464,929 A | 11/1995 | Bezwada |
| 5,522,899 A | 6/1996 | Michelson |
| 5,540,693 A | 7/1996 | Fisher |
| 5,595,751 A | 1/1997 | Bezwada |
| 5,597,579 A | 1/1997 | Bezwada |
| 5,601,561 A | 2/1997 | Terry |
| 5,607,687 A | 3/1997 | Bezwada |
| 5,618,552 A | 4/1997 | Bezwada |
| 5,620,698 A | 4/1997 | Bezwada |
| 5,645,850 A | 7/1997 | Bezwada |
| 5,648,088 A | 7/1997 | Bezwada |
| 5,658,335 A | 8/1997 | Allen |
| 5,665,122 A | 9/1997 | Kambin |
| 5,693,100 A | 12/1997 | Pisharodi |
| 5,698,213 A | 12/1997 | Jamiolkowski |
| 5,700,583 A | 12/1997 | Jamiolkowski |
| 5,725,531 A | 3/1998 | Shapiro |
| 5,857,995 A | 1/1999 | Thomas |
| 5,859,150 A | 1/1999 | Jamiolkowski |
| 5,916,228 A | 6/1999 | Ripich |
| 5,925,056 A | 7/1999 | Thomas |
| 5,976,187 A | 11/1999 | Richelsoph |
| 5,980,522 A | 11/1999 | Koros |
| 6,039,761 A | 3/2000 | Li |
| 6,045,579 A | 4/2000 | Hochshuler et al. |
| 6,053,922 A | 4/2000 | Krause |
| 6,056,763 A | 5/2000 | Parsons |
| 6,080,158 A | 6/2000 | Lin |
| 6,106,557 A | 8/2000 | Robioneck |
| 6,120,508 A | 9/2000 | Grunig |
| 6,126,689 A | 10/2000 | Brett |
| 6,139,558 A | 10/2000 | Wagner |
| 6,241,733 B1 | 6/2001 | Nicholson |
| 6,251,140 B1 | 6/2001 | Marino |
| 6,258,093 B1 | 7/2001 | Edwards |
| 6,296,644 B1 | 10/2001 | Saurat |
| D450,676 S | 11/2001 | Huttner |
| 6,342,074 B1 | 1/2002 | Simpson |
| 6,387,130 B1 | 5/2002 | Stone |
| 6,398,793 B1 | 6/2002 | McGuire |
| 6,409,766 B1 | 6/2002 | Brett |
| 6,436,101 B1 | 8/2002 | Hamada |
| 6,447,518 B1 | 9/2002 | Krause |
| 6,610,066 B2 | 8/2003 | Dinger |
| 6,635,060 B2 | 10/2003 | Hanson |
| RE38,335 E | 11/2003 | Aust |
| 6,641,582 B1 | 11/2003 | Hanson |
| 6,660,004 B2 | 12/2003 | Barker |
| 6,755,837 B2 | 6/2004 | Ebner |
| 6,764,491 B2 | 7/2004 | Frey |
| 6,840,941 B2 | 1/2005 | Rogers |
| 6,878,167 B2 | 4/2005 | Ferree |
| 6,949,108 B2 | 9/2005 | Holmes |
| 6,966,912 B2 | 11/2005 | Michelson |
| 7,018,415 B1 | 3/2006 | McKay |
| 7,060,073 B2 | 6/2006 | Frey |
| 7,070,598 B2 | 7/2006 | Lim |
| 7,087,055 B2 | 8/2006 | Lim |
| 7,125,424 B2 | 10/2006 | Banick |
| 7,226,482 B2 | 6/2007 | Messerli |
| 7,351,262 B2 | 4/2008 | Bindseil |
| 7,470,273 B2 | 12/2008 | Dougherty-Shah |
| 7,491,237 B2 | 2/2009 | Randall |
| 7,572,279 B2 | 8/2009 | Jackson |
| 7,575,580 B2 | 8/2009 | Lim |
| 7,578,820 B2 | 8/2009 | Moore |
| 7,601,173 B2 | 10/2009 | Messerli |
| 7,618,458 B2 | 11/2009 | Biedermann |
| 7,625,377 B2 | 12/2009 | Veldhuizen |
| 7,625,394 B2 | 12/2009 | Molz, IV |
| 7,666,186 B2 | 2/2010 | Harp |
| 7,674,265 B2 | 3/2010 | Smith |
| 7,682,400 B2 | 3/2010 | Zwirkoski |
| 7,771,473 B2 | 8/2010 | Thramann |
| 7,803,161 B2 | 9/2010 | Foley |
| 7,828,849 B2 | 11/2010 | Lim |
| 7,918,874 B2 | 4/2011 | Siegal |
| 7,922,719 B2 | 4/2011 | Ralph |
| 7,938,857 B2 | 5/2011 | Garcia-Bengochea |
| 7,963,967 B1* | 6/2011 | Woods ............................ 606/79 |
| 8,012,212 B2 | 9/2011 | Link |
| 8,025,697 B2 | 9/2011 | McClellan, III |
| 8,038,703 B2 | 10/2011 | Dobak, III |
| 8,043,293 B2 | 10/2011 | Warnick |
| 8,128,700 B2 | 3/2012 | Delurio |
| 8,216,317 B2 | 7/2012 | Thibodeau |
| 8,241,364 B2 | 8/2012 | Hansell |
| 8,343,222 B2 | 1/2013 | Cope |
| 8,579,981 B2 | 11/2013 | Lim |
| 8,628,577 B1* | 1/2014 | Jimenez .................... 623/17.15 |
| 8,663,331 B2 | 3/2014 | Mcclellan, III |
| 8,845,733 B2 | 9/2014 | O'Neil |
| 8,920,506 B2 | 12/2014 | McGuckin, Jr. |
| 8,940,050 B2 | 1/2015 | Laurence |
| 2002/0138078 A1 | 9/2002 | Chappuis |
| 2002/0165550 A1* | 11/2002 | Frey et al. ...................... 606/85 |
| 2002/0183758 A1* | 12/2002 | Middleton et al. .............. 606/79 |
| 2003/0135275 A1 | 7/2003 | Garcia |
| 2003/0191531 A1 | 10/2003 | Berry |
| 2004/0030387 A1 | 2/2004 | Landry |
| 2004/0059337 A1 | 3/2004 | Hanson |
| 2004/0068269 A1 | 4/2004 | Bonati |
| 2004/0083000 A1 | 4/2004 | Keller |
| 2004/0102784 A1 | 5/2004 | Pasquet |
| 2004/0102846 A1 | 5/2004 | Keller |
| 2004/0127990 A1 | 7/2004 | Bartish |
| 2004/0147129 A1 | 7/2004 | Rolfson |
| 2004/0220668 A1 | 11/2004 | Eisermann |
| 2005/0038431 A1 | 2/2005 | Bartish |
| 2005/0096745 A1 | 5/2005 | Andre |
| 2005/0149034 A1 | 7/2005 | Assell |
| 2005/0165420 A1* | 7/2005 | Cha ............................. 606/150 |
| 2005/0171541 A1 | 8/2005 | Boehm |
| 2005/0177173 A1 | 8/2005 | Aebi |
| 2005/0240193 A1 | 10/2005 | Layne |
| 2006/0036244 A1 | 2/2006 | Spitler |
| 2006/0058807 A1 | 3/2006 | Landry |
| 2006/0064101 A1* | 3/2006 | Arramon ........................ 606/82 |
| 2006/0064102 A1 | 3/2006 | Ebner |
| 2006/0069436 A1 | 3/2006 | Sutton |
| 2006/0074429 A1 | 4/2006 | Ralph |
| 2006/0100622 A1 | 5/2006 | Jackson |
| 2006/0111715 A1 | 5/2006 | Jackson |
| 2006/0111728 A1 | 5/2006 | Abdou |
| 2006/0129244 A1 | 6/2006 | Ensign |
| 2006/0142858 A1 | 6/2006 | Colleran |
| 2006/0167547 A1 | 7/2006 | Suddaby |

(56) References Cited

U.S. PATENT DOCUMENTS

| | | |
|---|---|---|
| 2006/0189999 A1 | 8/2006 | Zwirkoski |
| 2006/0212118 A1 | 9/2006 | Abernathie |
| 2006/0229627 A1 | 10/2006 | Hunt |
| 2006/0235426 A1 | 10/2006 | Lim |
| 2006/0253120 A1 | 11/2006 | Anderson |
| 2006/0254784 A1 | 11/2006 | Hartmann et al. |
| 2006/0265077 A1 | 11/2006 | Zwirkoski |
| 2006/0293753 A1 | 12/2006 | Thramann |
| 2007/0055264 A1 | 3/2007 | Parmigiani |
| 2007/0067035 A1 | 3/2007 | Falahee |
| 2007/0093897 A1 | 4/2007 | Gerbec |
| 2007/0142843 A1 | 6/2007 | Dye |
| 2007/0162132 A1 | 7/2007 | Messerli |
| 2007/0213737 A1 | 9/2007 | Schermerhorn |
| 2007/0213826 A1 | 9/2007 | Smith |
| 2007/0225726 A1 | 9/2007 | Dye |
| 2007/0225815 A1 | 9/2007 | Keith |
| 2007/0233130 A1 | 10/2007 | Suddaby |
| 2007/0260314 A1 | 11/2007 | Biyani |
| 2007/0270957 A1 | 11/2007 | Heinz |
| 2007/0270968 A1 | 11/2007 | Baynham |
| 2008/0027544 A1 | 1/2008 | Melkent |
| 2008/0027550 A1 | 1/2008 | Link |
| 2008/0045966 A1 | 2/2008 | Buttermann |
| 2008/0051890 A1 | 2/2008 | Waugh |
| 2008/0058933 A1 | 3/2008 | Garner |
| 2008/0065082 A1 | 3/2008 | Chang |
| 2008/0077150 A1 | 3/2008 | Nguyen |
| 2008/0077241 A1 | 3/2008 | Nguyen |
| 2008/0082173 A1 | 4/2008 | Delurio |
| 2008/0091211 A1 | 4/2008 | Gately |
| 2008/0097454 A1 | 4/2008 | DeRidder |
| 2008/0108990 A1 | 5/2008 | Mitchell |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately |
| 2008/0154379 A1 | 6/2008 | Steiner |
| 2008/0208255 A1 | 8/2008 | Siegal |
| 2008/0221586 A1 | 9/2008 | Garcia-Bengochea |
| 2008/0221687 A1 | 9/2008 | Viker |
| 2008/0234732 A1 | 9/2008 | Landry |
| 2008/0234733 A1 | 9/2008 | Scrantz |
| 2008/0243126 A1 | 10/2008 | Gutierrez |
| 2008/0243255 A1 | 10/2008 | Butler |
| 2008/0249628 A1 | 10/2008 | Altarac |
| 2008/0255563 A1 | 10/2008 | Farr |
| 2008/0255574 A1 | 10/2008 | Dye |
| 2008/0269904 A1 | 10/2008 | Voorhies |
| 2008/0312743 A1 | 12/2008 | Vila |
| 2009/0030423 A1 | 1/2009 | Puno |
| 2009/0054898 A1 | 2/2009 | Gleason |
| 2009/0054911 A1 | 2/2009 | Mueller |
| 2009/0062807 A1 | 3/2009 | Song |
| 2009/0076607 A1 | 3/2009 | Aalsma |
| 2009/0112217 A1 | 4/2009 | Hester |
| 2009/0143859 A1 | 6/2009 | McClellan, III |
| 2009/0182431 A1 | 7/2009 | Butler |
| 2009/0192616 A1 | 7/2009 | Zielinski |
| 2009/0216234 A1 | 8/2009 | Farr |
| 2009/0234364 A1 | 9/2009 | Crook |
| 2009/0240335 A1 | 9/2009 | Arcenio |
| 2009/0276049 A1 | 11/2009 | Weiland |
| 2009/0299479 A1 | 12/2009 | Jones |
| 2010/0016968 A1 | 1/2010 | Moore |
| 2010/0030217 A1 | 2/2010 | Mitusina |
| 2010/0076502 A1 | 3/2010 | Guyer |
| 2010/0094422 A1 | 4/2010 | Hansell |
| 2010/0100098 A1* | 4/2010 | Norton et al. ............. 606/80 |
| 2010/0125334 A1 | 5/2010 | Krueger |
| 2010/0161060 A1* | 6/2010 | Schaller et al. ......... 623/17.16 |
| 2010/0174321 A1 | 7/2010 | Schaller |
| 2010/0185290 A1 | 7/2010 | Compton |
| 2010/0191241 A1 | 7/2010 | McCormack |
| 2010/0198263 A1 | 8/2010 | Siegal |
| 2010/0211076 A1* | 8/2010 | Germain et al. ............. 606/84 |
| 2010/0211107 A1 | 8/2010 | Muhanna |
| 2010/0217269 A1 | 8/2010 | Landes |
| 2010/0234849 A1 | 9/2010 | Bouadi |
| 2010/0249935 A1 | 9/2010 | Slivka |
| 2010/0256768 A1 | 10/2010 | Lim |
| 2010/0280619 A1 | 11/2010 | Yuan |
| 2010/0305700 A1 | 12/2010 | Ben-Arye |
| 2010/0305704 A1 | 12/2010 | Messerli |
| 2010/0331845 A1 | 12/2010 | Foley |
| 2011/0004216 A1 | 1/2011 | Amendola |
| 2011/0009970 A1 | 1/2011 | Puno |
| 2011/0029083 A1 | 2/2011 | Hynes |
| 2011/0029085 A1 | 2/2011 | Hynes |
| 2011/0035011 A1 | 2/2011 | Cain |
| 2011/0106260 A1 | 5/2011 | Laurence |
| 2011/0112586 A1 | 5/2011 | Guyer |
| 2011/0125266 A1 | 5/2011 | Rodgers |
| 2011/0276142 A1 | 11/2011 | Niemiec |
| 2011/0282459 A1 | 11/2011 | McClellan, III |
| 2011/0301712 A1 | 12/2011 | Palmatier et al. |
| 2011/0319898 A1 | 12/2011 | O'Neil |
| 2011/0319899 A1 | 12/2011 | O'Neil |
| 2011/0319998 A1 | 12/2011 | O'Neil |
| 2011/0319999 A1 | 12/2011 | O'Neil |
| 2011/0320000 A1 | 12/2011 | O'Neil |
| 2012/0035730 A1 | 2/2012 | Spann |
| 2012/0209383 A1 | 8/2012 | Tsuang |
| 2012/0277877 A1 | 11/2012 | Smith |
| 2013/0006362 A1 | 1/2013 | Biedermann |
| 2013/0023937 A1 | 1/2013 | Biedermann |
| 2013/0035762 A1 | 2/2013 | Siegal |
| 2013/0109925 A1 | 5/2013 | Horton |
| 2013/0116791 A1 | 5/2013 | Theofilos |
| 2013/0138214 A1 | 5/2013 | Greenhalgh |
| 2013/0150906 A1 | 6/2013 | Kerboul |
| 2013/0173004 A1 | 7/2013 | Greenhalgh |
| 2013/0238006 A1 | 9/2013 | O'Neil |
| 2013/0268077 A1 | 10/2013 | You |
| 2013/0310937 A1 | 11/2013 | Pimenta |
| 2014/0025170 A1 | 1/2014 | Lim |
| 2014/0039626 A1 | 2/2014 | Mitchell |
| 2014/0058512 A1 | 2/2014 | Petersheim |
| 2014/0058513 A1 | 2/2014 | Gahman |
| 2014/0172103 A1 | 6/2014 | O'Neil |
| 2014/0172105 A1 | 6/2014 | Frasier |
| 2015/0032212 A1 | 1/2015 | O'Neil |

FOREIGN PATENT DOCUMENTS

| | | |
|---|---|---|
| EP | 1283026 | 9/2003 |
| EP | 1405602 | 4/2004 |
| EP | 1605836 | 12/2005 |
| EP | 1308132 | 12/2006 |
| EP | 1829486 | 9/2007 |
| FR | 2874814 | 3/2006 |
| FR | 2948277 | 1/2011 |
| WO | WO 9214423 | 9/1992 |
| WO | WO 9834568 | 8/1998 |
| WO | 9963914 | 12/1999 |
| WO | WO 9960956 | 12/1999 |
| WO | 0024343 | 5/2000 |
| WO | WO 0203870 | 1/2002 |
| WO | WO 03003951 | 1/2003 |
| WO | WO 2004080316 | 9/2004 |
| WO | 2004069033 | 1/2005 |
| WO | 2006118944 | 11/2006 |
| WO | 2006044920 | 12/2006 |
| WO | 2008005627 | 1/2008 |
| WO | WO 2006072941 A3 | 7/2008 |
| WO | WO 2010011348 | 1/2010 |
| WO | WO 2010075555 | 10/2010 |
| WO | WO 2010121002 | 12/2010 |
| WO | 2011013047 | 4/2011 |
| WO | WO 2011060087 | 5/2011 |
| WO | WO 2012027490 | 3/2012 |
| WO | WO 2012103254 | 8/2012 |
| WO | 2012129197 | 9/2012 |
| WO | 2013149611 | 10/2013 |

(56) References Cited

FOREIGN PATENT DOCUMENTS

OTHER PUBLICATIONS

Vandorpe, "Biodegradable Polyphosphazenes for Biomedical Applications"; *Handbook of Biodegradable Polymers*; 1997; pp. 161-182; Hardwood Academic Press.

Allcock, "Polyphosphazenes"; *The Encyclopedia of Polymer Science*; 1988; pp. 31-41; vol. 13; Wiley Intersciences, John Wiley & Sons.

Cohn, "Polymer Preprints"; *Journal of Biomaterials Research*; 1989; p. 498; Biomaterials Research Labortatory, Casali Institute of Applied Chemistry, Israel.

Cohn, "Biodegradable PEO/PLA Block Copolymers"; *Journal of Biomedical Materials Research*; 1988; pp. 993-1009; vol. 22; John Wiley & Sons, Inc.

Heller, "Poly (Otrho Esters)"; *Handbook of Biodegradable Polymers*; edited by Domb; et al; Hardwood Academic Press; 1997; pp. 99-118.

Kemnitzer, "Degradable Polymers Derived From the Amino Acid L-Tyrosine"; 1997; pp. 251-272; edited by Domb, et. al., Hardwood Academic Press.

Khoo, "Minimally Invasive Correction of Grade I and II Isthmic Spondylolisthesis using AxiaLIF for L5/S1 Fusion", pp. 1-7, Rev B Sep. 15, 2008.

U.S. Appl. No. 61/009,546, filed Dec. 28, 2007 Rodgers.

U.S. Appl. No. 61/140,926, filed Dec. 26, 2008 Spann.

U.S. Appl. No. 61/178,315, filed May 14, 2009 Spann.

* cited by examiner

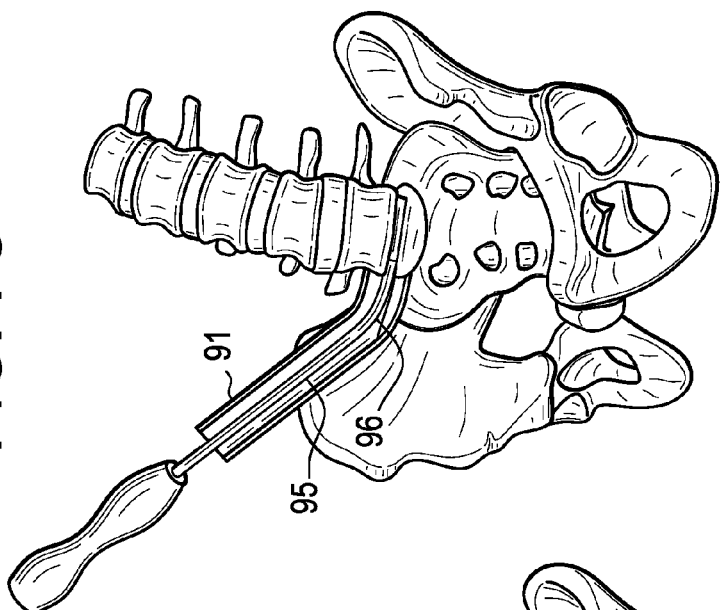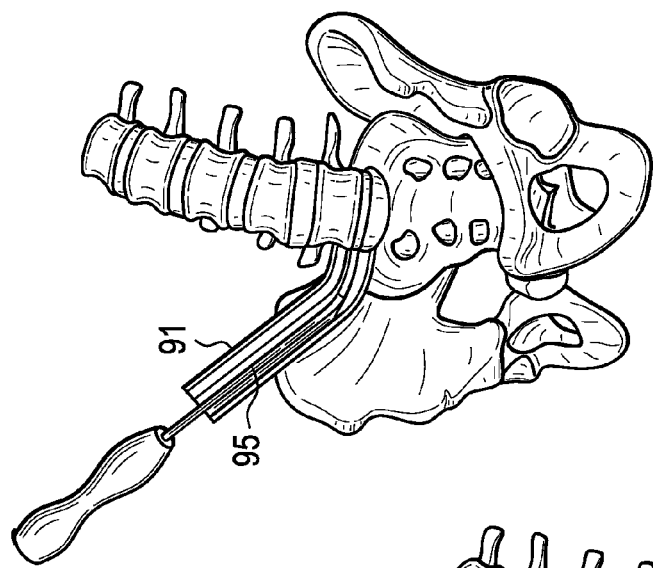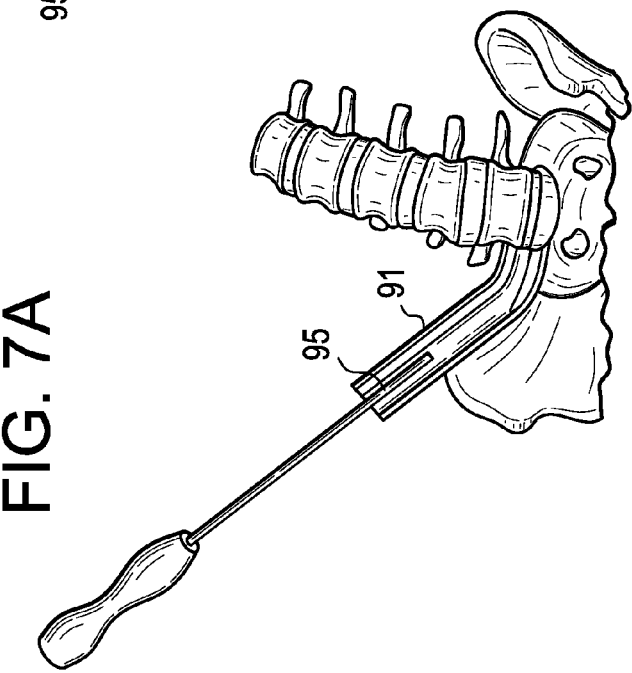

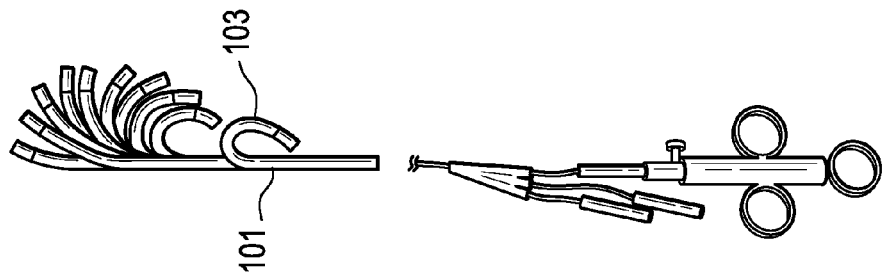
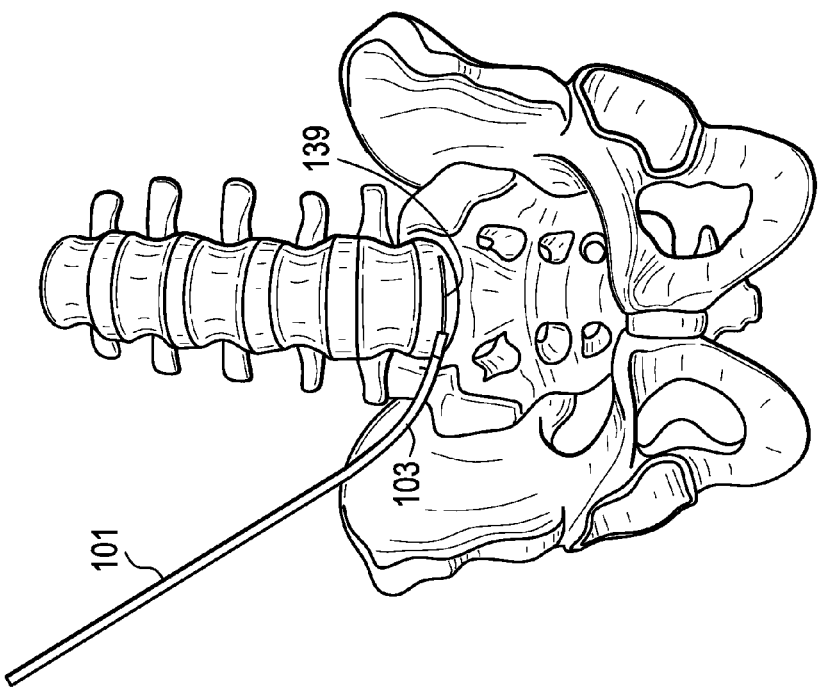
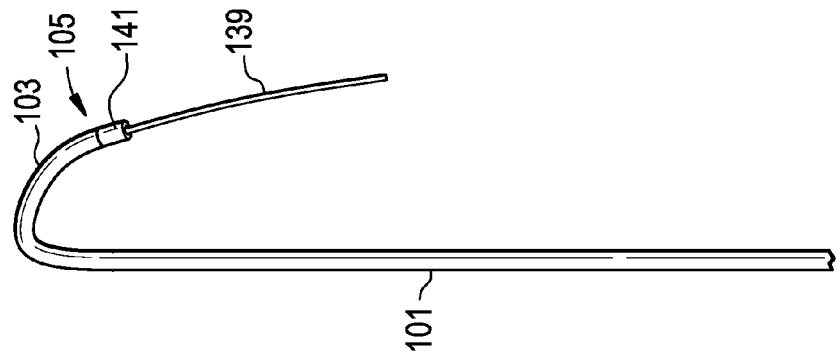

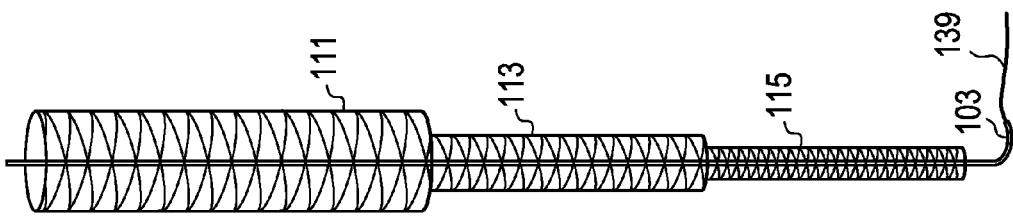
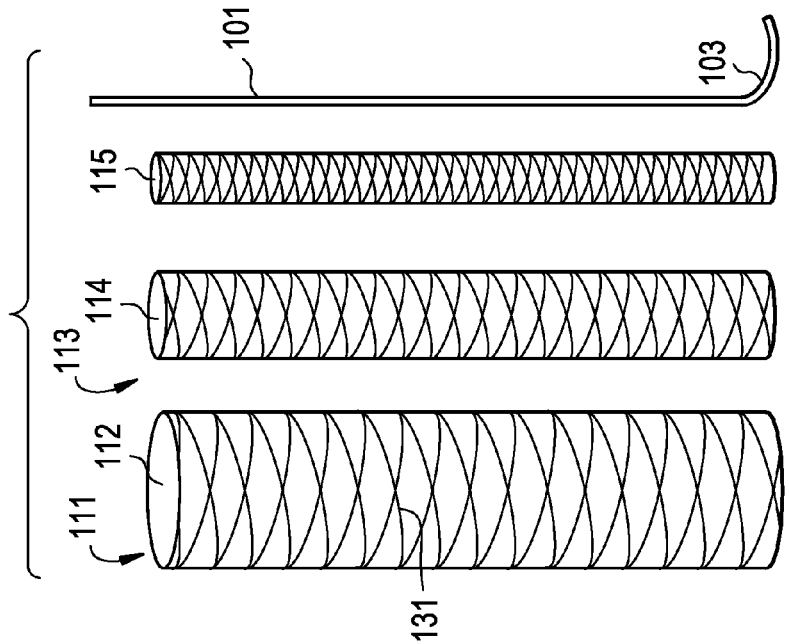

INSTRUMENTS AND METHODS FOR NON-PARALLEL DISC SPACE PREPARATION

CONTINUING DATA

This application claims priority from U.S. Ser. No. 61/358,220, filed on Jun. 24, 2010, and entitled "Instruments and Methods for Non-Parallel Disc Space Preparation", the specifications of which is incorporated by reference in its entirety.

This application claims priority from U.S. Ser. No. 61/379,194, filed on Sep. 1, 2010, and entitled "Flexible Vertebral Body Shavers", and is related to non-provisional U.S. Ser. No. 13/163,496, filed on even date, entitled "Flexible Vertebral Body Shavers", the specifications of which are incorporated by reference in their entireties.

This application claims priority from provisional application U.S. Ser. No. 61/385,958, filed Sep. 23, 2010, and entitled "Multi-Segment Lateral Cages adapted to Flex Substantially in the Coronal Plane", the specification of which is incorporated by reference in its entirety.

This application claims priority from provisional application U.S. Ser. No. 61/410,177, filed Nov. 4, 2010, and entitled "Multi-Segment Lateral Cages adapted to Flex Substantially in the Coronal Plane", the specification of which is incorporated by reference in its entirety.

This application is related to non-provisional U.S. Ser. No. 13/163,517, filed on even date, entitled "Multi-Segment Lateral Cages adapted to Flex Substantially in the Coronal Plane", the specification of which is incorporated by reference in its entirety.

This application claims priority from provisional application U.S. Ser. No. 61/397,716, filed Nov. 30, 2010, and entitled "Lateral Spondylolisthesis Reduction Cage", and is related to non-provisional U.S. Ser. No. 13/163,427, filed on even date, entitled "Lateral Spondylolisthesis Reduction Cage", the specifications of which are incorporated by reference in their entireties.

This application claims priority from provisional application U.S. Ser. No. 61/466,302, filed Mar. 22, 2011, and entitled "Universal Trial for Cages", and is related to non-provisional U.S. Ser. No. 13/163,397, filed on even date, entitled "Universal Trial for Cages", the specifications of which are incorporated by reference in their entireties.

BACKGROUND OF THE INVENTION

The lateral access approach is frequently utilized to deliver interbody fusion cages to the lumbar spine. In comparison to conventional anterior or posterior approaches to the lumbar spine, the lateral approach is thought to minimize posterior and/or anterior tissue damage as well as reduce surgery time, associated blood loss, and infection risk.

When multi-level access to the spine is provided through a single minimal access port, the insertion trajectory to the superior and inferior levels is not parallel to those levels. In addition, direct lateral access parallel to the L4/5 and L5/S1 levels is prevented by the presence of the iliac crest.

Accordingly, the angled trajectory required for lateral access to these lower levels requires the cages to be implanted at a "malpositioned" angle that prevents balanced loading across the vertebral endplates and spine. See FIG. 1. This "malpositioned" access, associated endplate damage and device placement can initiate subsidence and spinal instability.

Current spreader and shaver technology includes varying paddle shapes and cutting geometries with rigid drive shafts.

US Patent Publication No. 2008-00445966 discloses a chisel cutting guide for excising a portion of a vertebral body.

Conventional dilation systems used in intervertebral fusion procedures are typically rigid and non-steerable. Accordingly, they require a line of sight insertion towards the target disc.

US Patent Publication No. US 2007-0225815 (Annulex) discloses a curved stylet for steering within a disc space Annulex does not disclose an assembly comprising a curved guide wire and a flexible dilator tube.

SUMMARY OF THE INVENTION

The present inventors have developed flexible shavers and curved access ports that reduce the above-mentioned access and trajectory problems associated with conventional lateral approaches to the lower spine. The devices and methods of the present invention allow the surgeon to present disc preparation instruments to a disc space in the lower spine in a manner that is parallel to the disc space. Consequently, these devices and methods allow for preparing with less endplate damage and higher preparation symmetry.

Therefore, in accordance with the present invention there is provided a flexible shaver for preparing a vertebral endplate, comprising:
   a) a shaft having a proximal end portion and a distal end portion,
   b) a handle attached to the proximal end portion of the shaft, and
   c) a shaving head attached to the distal end portion of the shaft, the head comprising:
      i) an body portion;
      ii) a first face forming a first cutting edge, and
wherein the shaft and head comprise a universal joint.

Also in accordance with the present invention there is provided a method of intervertebral disc space preparation, comprising the steps of:
   a) selecting a shaver having a flexible shaft;
   b) inserting the shaver into an intervertebral disc space bounded by opposed vertebral endplates, and
   c) contacting the shaver to a vertebral endplate.

Also in accordance with the present invention there is provided a method of preparing an intervertebral disc space between opposing vertebral endplates, comprising the steps of:
   a) inserting a curved (preferably flexible) port into a lateral aspect of the disc space, the curved port having a bore.

Also in accordance with the present invention there is provided a assembly comprising:
   a) a curved port having a bore having a transverse cross-section; and
   b) a vertebral endplate shaver having a transverse cross-section,
wherein the shaver is disposed within the bore of the curved port,
wherein the transverse cross-section of the bore substantially corresponds to the transverse cross-section of the shaver so as to determine the orientation of the shaver within the bore.

Also in accordance with the present invention there is provided a port for use in preparing an intervertebral disc space, comprising:
   a) an outer cannula having a bore, and
   b) an inner cannula having a bore having a non-circular transverse cross-section,
wherein the inner cannula is disposed within the bore of the outer cannula.

Also in accordance with the present invention there is provided a port for use in preparing an intervertebral disc space, the port comprising a longitudinal bore therethrough, the bore having a proximal end portion having a transverse cross-section and a distal end portion having a transverse cross-section, wherein the transverse cross-section of the proximal end portion of the bore is greater than that transverse cross-section of the distal end portion of the bore.

Also in accordance with the present invention there is provided a port for use in preparing an intervertebral disc space, comprising:
 a) an outer cannula having a bore having a proximal end portion and a distal end portion,
 b) an upper insert disposed at least in the distal end portion of the bore, and
 c) a lower insert disposed at least in the distal end portion of the bore.

Also in accordance with the present invention there is provided a assembly for providing access to an intervertebral disc, comprising;
 a) a catheter having a steerable tip,
 b) a first flexible dilator tube having a first bore defining a first longitudinal axis,
 c) a second flexible dilator tube having a second bore defining a second longitudinal axis,
wherein the first flexible dilator tube is received with the bore of the second flexible dilator tube, and
wherein the steerable tip is received within the bore of the first flexible dilator tube.

Also in accordance with the present invention there is provided a method of accessing a target intervertebral disc, comprising the steps of:
 a) advancing a steerable catheter having a tip through an incision and towards the target disc,
 b) imparting a first curve in the tip of the steerable catheter,
 c) docking the curved tip upon the target disc,
 d) advancing a first flexible dilator tube over the curved tip to impart a first curve in the first flexible dilator tube.

The present invention also relates to an assembly comprising a steerable, curvable guide wire and a set of flexible dilator tubes having sequentially increasing bore diameters. When a flexible dilator tube is passed over the curved guide wire, the flexible dilator tube curves in an arc substantially similar to that of the curved guide wire. Thus, the set of curved dilator tubes can open up a curved access path to the L4/5 and L5/S1 levels that previously could not be directly accessed due to the presence of the iliac crest.

Also in accordance with the present invention there is provided a flexible shaver for preparing a vertebral endplate, comprising:
 a) a shaft having a proximal end portion and a distal end portion,
 b) a handle attached to the proximal end portion of the shaft, and
 c) a shaving head attached to the distal end portion of the shaft, the head comprising:
  i) an body portion;
  ii) a first face forming a first cutting edge, and
wherein the shaft comprises a flexible portion.

Also in accordance with the present invention there is provided a method of performing a procedure on a spine, comprising the step of:
 a) advancing an instrument along a curved path, the path being substantially in a coronal plane, towards a lateral aspect of an intervertebral disc.

DESCRIPTION OF THE FIGURES

FIGS. 7a-c disclose advancing a shaver through the docked port of FIG. 6c.

FIG. 9a discloses a steerable catheter having a guide wire extending therefrom.

FIG. 9b discloses the steerable catheter of FIG. 9a docked onto a spine.

FIG. 9c discloses a steerable catheter displaying various degrees of curved tips.

FIG. 10a discloses three flexible dilation tubes and a steerable catheter.

FIG. 10b discloses an assembly of three flexible dilation tubes and a steerable catheter.

DETAILED DESCRIPTION OF THE INVENTION

Figure 1:
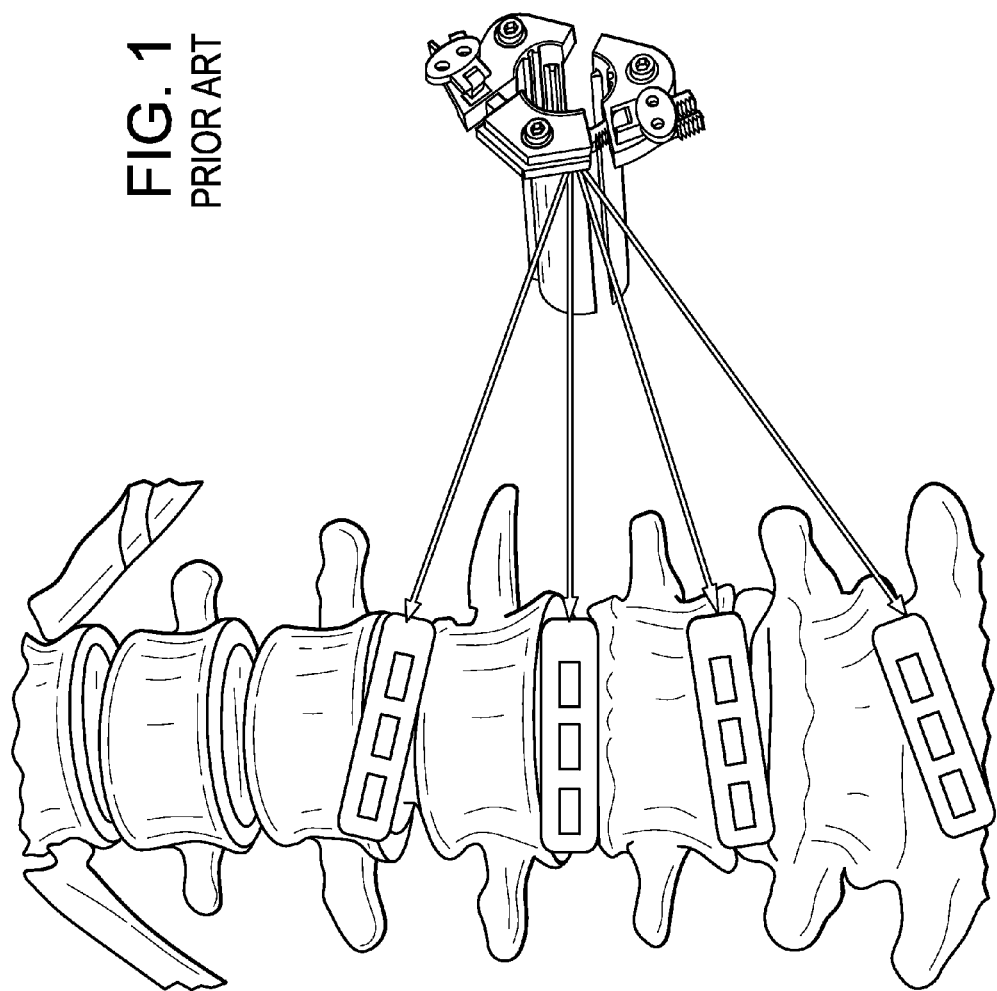
FIG. 1 discloses a coronal view of a human spine in which a a conventional method of laterally implanting cages in the lower spine is used, producing malpositioned cages.

The present invention relates to flexible spreaders and shaver devices and methods for parallel preparation of an intervertebral disc space in the context of a non-parallel access trajectory. The flexible shavers utilize curved guide tubes to enable their placement, insertion, flexing, bending and/or pivoting in the disc space.

In some embodiments, the flexible shaft can have a flexibility-imparting geometry that includes use of at least one of a) a spring (available from SS White of Piscataway, N.J.), b) a slotted tube (available from Necomed of Hicksville, Ohio), and c) a standard universal joint. Now referring to FIGS. 2a -e, in some embodiments, the flexible shaver 11 of this embodiment also includes a proximal handle 15, an intermediate shaft 19 comprising a universal joint 20, and a distal shaver head 23.

Therefore, now referring to FIGS. 2a-e, there is provided a flexible shaver 11 for preparing a vertebral endplate, comprising:

a) a shaft 19 having a proximal end portion 21 and a distal end portion 22, b) a handle 15 attached to the proximal end portion of the shaft, and c) a shaving head 23 attached to the distal end portion of the shaft, the head comprising:

i) an body portion 24;

ii) a first face 25 forming a first cutting edge, and wherein the shaft comprises a universal joint 20.

Figure 2A:
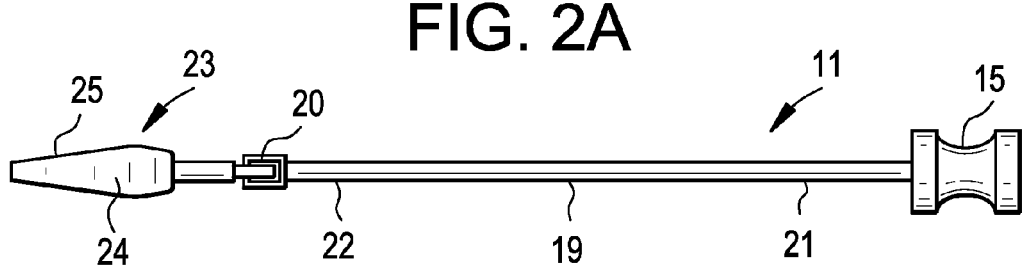
FIG. 2a-c discloses various shavers of the present invention having a universal joint, wherein the shavers are presented in varying degrees of angulation.
Figure 2B:
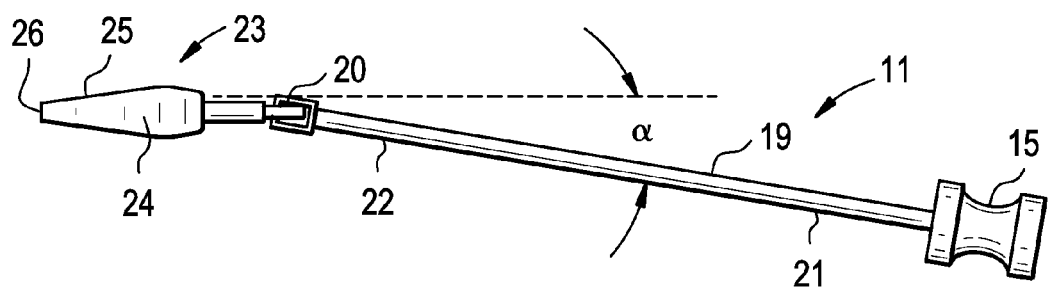
Figure 2C:
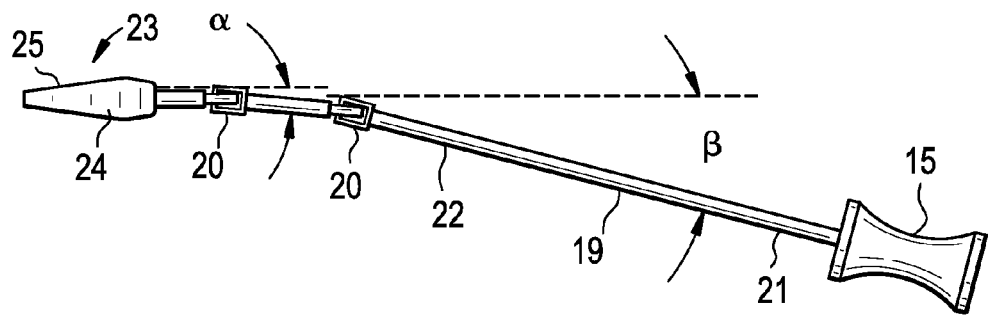
Figure 2D:
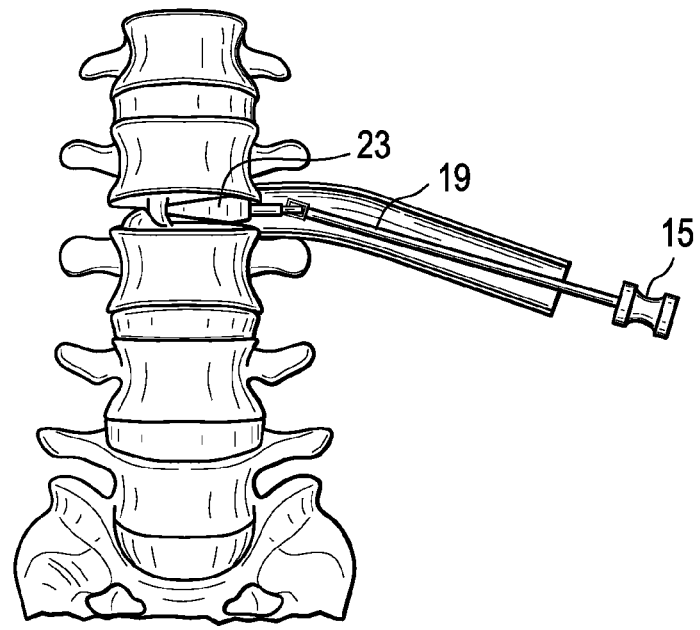
FIG. 2d-e discloses a universal jointed shaver of the present invention preparing an endplate in the lower spine through a port of the present invention.
Figure 2E:
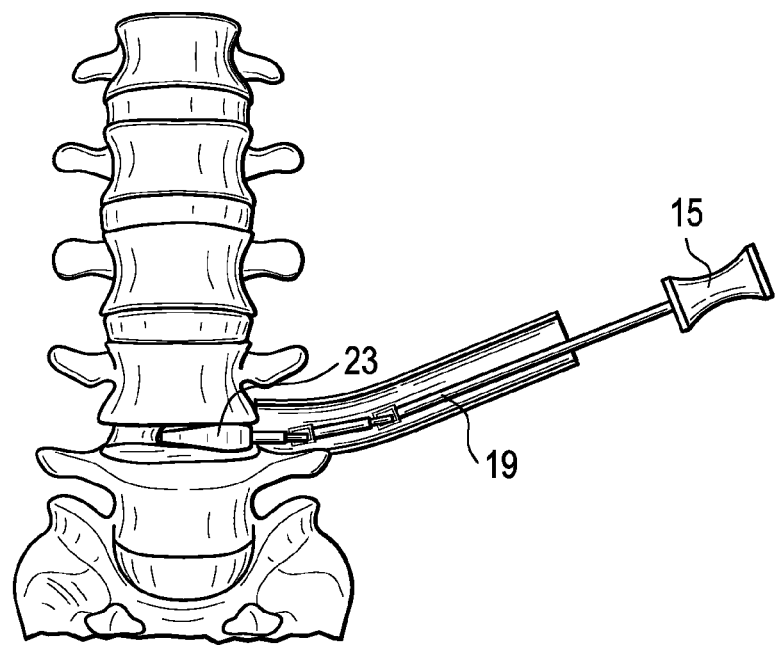

FIG. 2d and 2e shows flexible shavers 11 of this embodiment disposed within respective disc spaces, wherein the shaving heads are disposed parallel to the disc space. Therefore, use of the shaver results in shaved endplates that are substantially parallel to the natural endplates, and so will easily accommodate a lateral fusion cage without causing asymmetry.

The flexible spreader/shaver comprises a distal rigid or non-rigid shaver head having a blade. This shaver head is attached to a partially flexible drive shaft that is in turn connected to a proximal handle. The handle is rotated to turn the drive shaft and the shaving head. The flexible shaft allows variable angulations of the handle relative to the shaver blade, thereby allowing the surgeon to use an angled approach to prepare the disc space in a manner that nonetheless keeps the shaving head substantially parallel to the disc space. Typically, the shaver angulation angle α relative to the drive shaft can be up to 90 degrees, but is preferably between 10 and 45 degrees. In some embodiments, the shaving head of the flexible shaver has a bullet tip 26 for ease of entry into the disc space.

Figure 3A:
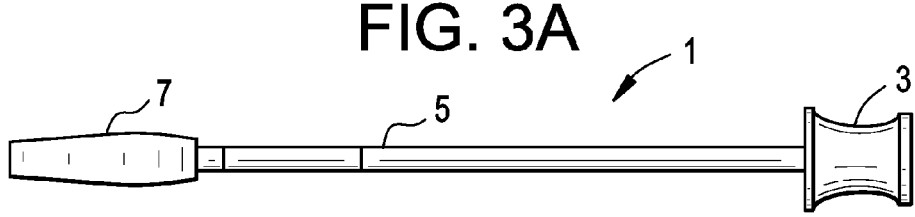
FIG. 3a-b discloses various shavers of the present invention having a bendable shaft, wherein the shavers are presented in varying degrees of angulation.
Figure 3B:
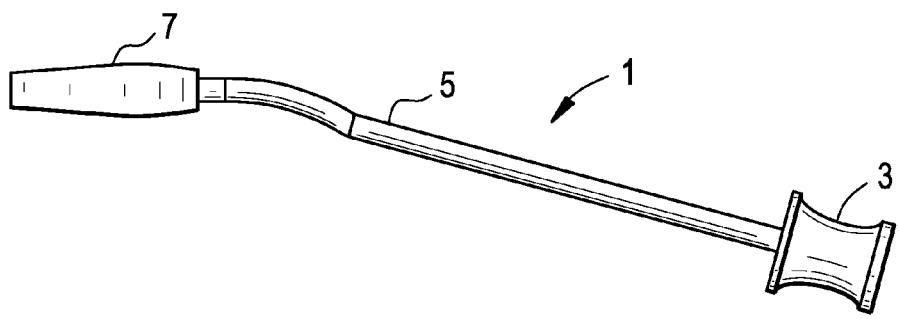
Figure 3C:
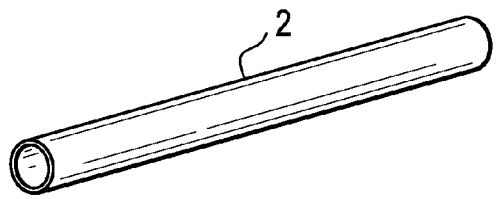
FIG. 3c-d disclose a flexible port in its straight and curved configuration.

Now referring to FIGS. 3a-c, in some embodiments, the flexible shaver 1 of the present invention includes a proximal handle 3, an intermediate flexible shaft 5, and a distal shaver head 7. The flexible shaft can be a solid shaft made from a flexible material, or can be aa spring (available from SS White of Piscataway, N.J.), or a slotted tube (available from Necomed of Hicksville, Ohio). Such flexible materials include metals such as nitinol, and polymers such as polyether ether ketone (PEEK), acrylonitrile butadiene styrene (ABS), polypropylene, and polyethylene. Stainless steels, titanium alloys, cobalt chromium alloys or combinations, mixtures and/or blends thereof. The flexible shaft may be the flexible material itself or the shaft may be constructed of strands which are wound or shafts which are slotted to impart flexibility. FIGS. 3 a-b show a flexible shaver having a shaft made of a flexible material in its straight and curved configurations, respectively. FIG. 3c shows two flexible shavers 1 of this embodiment disposed at least partially within respective disc spaces, wherein each shaving head is disposed parallel to the disc space.

Therefore, now referring to FIG. 3a-c, there is provided a method of intervertebral disc space preparation, comprising the steps of:

a) selecting a shaver having a flexible shaft;

b) inserting the shaver into an intervertebral disc space bounded by opposed vertebral endplates, and c) contacting the shaver to a vertebral endplate to cut the endplate.

As shown in FIG. 3c, the use of the flexible shaver allows the shaving head to be essentially parallel to the opposed vertebral endplates. Thus, when the shaver is rotated about its longitudinal axis, the shaving head cuts in a manner parallel to the endplates, thereby preserving symmetry about the disc space.

The flexible shaft can be made flexible in many different ways. For example, in some embodiments, the flexible shaft is made of a flexible material. In other embodiments, the geometry of the shaft imparts flexibility thereto. In some embodiments thereof, the flexible shaft has a universal joint. In other such embodiments, the flexible shaft is slotted to impart flexibility. In other such embodiments, the flexible shaft comprises a spring.

Figure 3D:
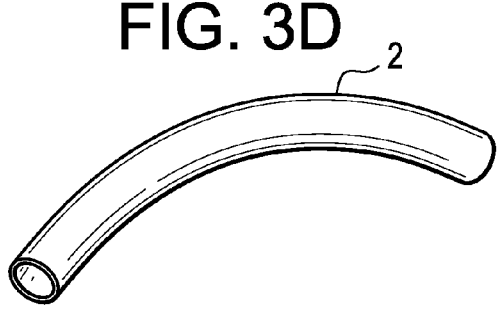

FIGS. 3c-d disclose a flexible port 2 in its straight and curved configuration.

Figure 4A:
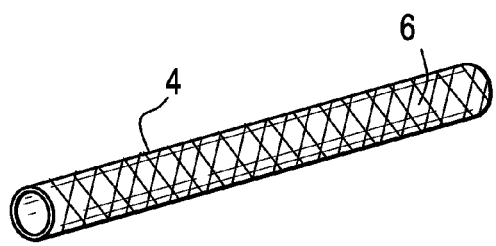
FIGS. 4a-4b disclose a reinforced flexible port in its straight and curved configuration.
Figure 4B:
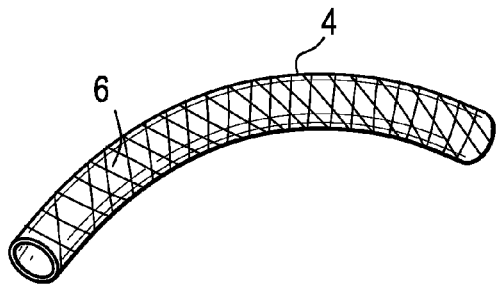

FIGS. 4a-4b disclose a flexible port 4 having reinforcements 6, the port being in its straight and curved configuration.

Figure 4C:
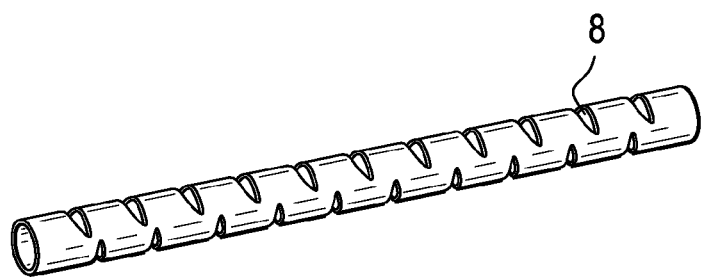
FIGS. 4c-4d disclose a slotted port in its straight and curved configuration.
Figure 4D:
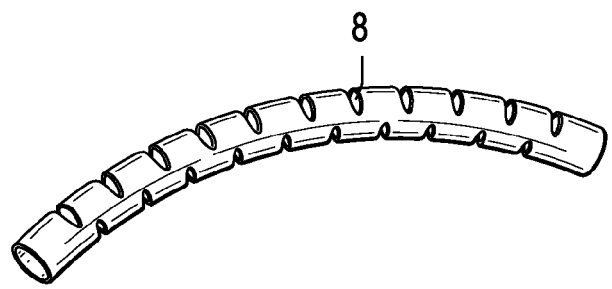

FIGS. 4c-4d disclose a port having slots 8 in its straight and curved configuration.

In some embodiments, a flexible port is used to dock onto a bone adjacent the disc space and thereby guide disc space preparation instruments into the disc space in a minimally invasive manner. The flexibility allows the port to curve at its distal end portion to produce a curve having an angle of, for example, 20 degrees. This curve allows a shaver to enter the port at a downward trajectory (which occurs when using a single spinal access site for multiple levels) and then orient parallel to the endplates (in order to best prepare the endplates). In some embodiments, the angle of the shaver is between 10 and 45 degrees.

Figure 5A:
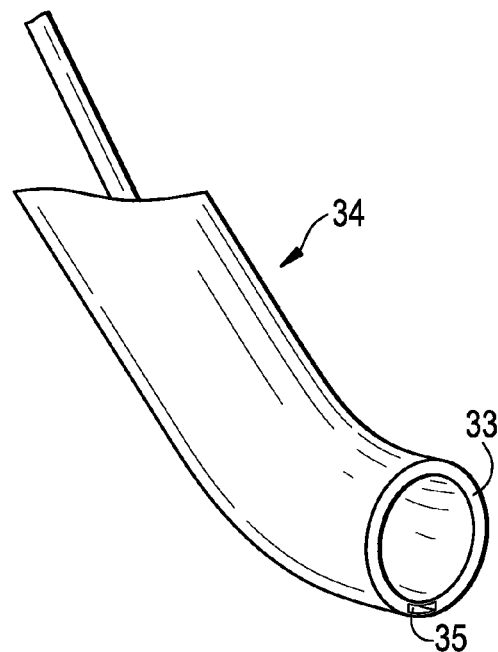
FIGS. 5a and b present a perspective view of a port of the present invention, wherein the securement feature is respectively retracted and advanced.
Figure 5B:
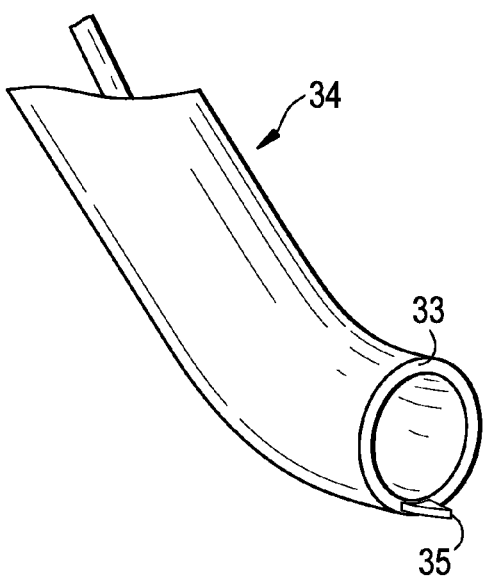

Now referring to FIGS. 5a-b, in some embodiments, the port may include one or more fixed or actuatable securement features 35, including a spike or teeth, extending from its distal end portion 33. These securement features fix to the bone and thereby insure secure docking of the port adjacent the target disc space. FIGS. 5a and b present a perspective view of a port of the present invention, wherein the securement feature 35 is respectively retracted and advanced.

Figure 6C:
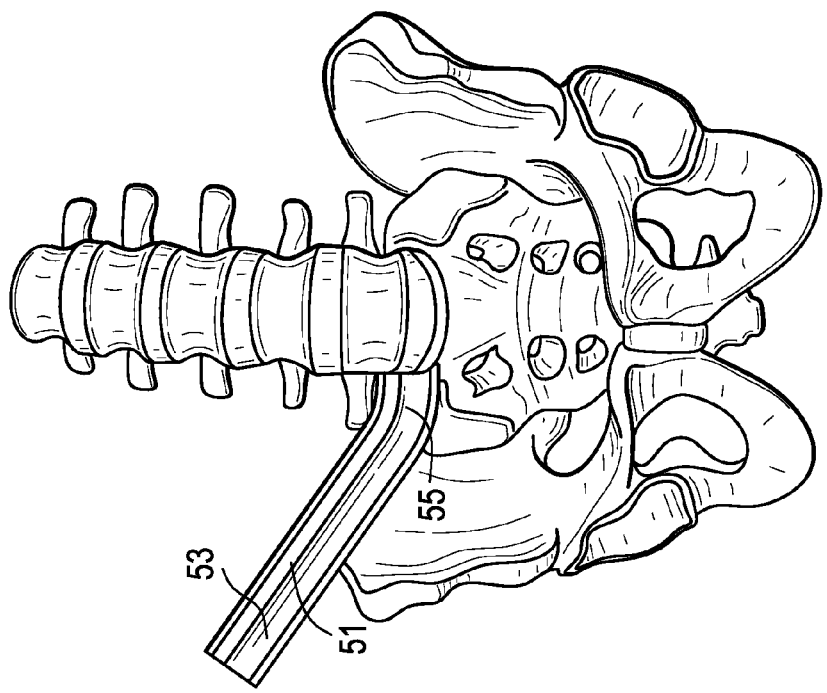
FIG. 6c presents the port of FIG. 6b laterally docked onto the lower spine.
Figure 6A:
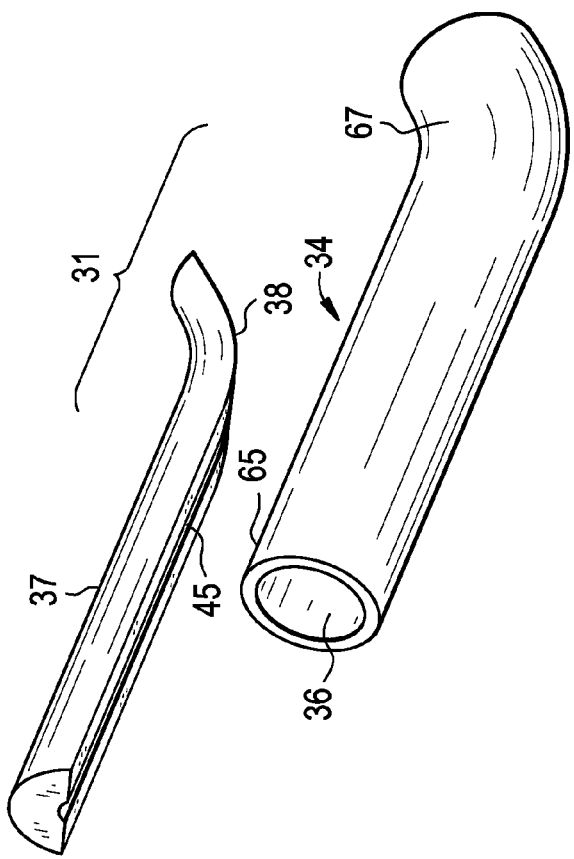
FIG. 6a presented an exploded version of a port of the present invention comprising an outer cannula and an upper insert.
Figure 6B:
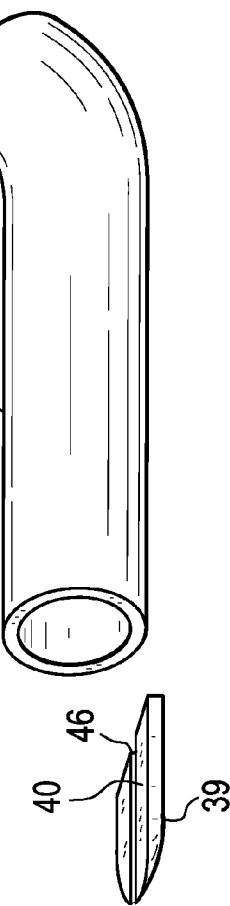
FIG. 6b presented an assembled version of a port of the present invention comprising an outer cannula and an upper and lower insert.

Now referring to FIG. 6a-c, in some embodiments, the port 31 may comprise an outer cannula 34 and inserts 37 and 39. These inserts may, when installed, form an inner cannula that helps fix the orientation of the shaver when the shaver passes therethrough. Therefore, in some embodiments thereof, there is provided a port for use in preparing an intervertebral disc space, which comprises:

a) an outer cannula 34 having a bore, and b) an inner cannula having a bore having a non-circular transverse cross-section, wherein the inner cannula is disposed within the bore of the outer cannula.

Preferably, the port further has features that allow it to securely dock onto the vertebral bone adjacent the disc space. Preferably, this comprises a securement feature disposed upon a distal end portion of at least one of the outer cannula and inner cannula.

In some embodiments, the port having the inner and outer cannulae has a distal end portion that is curved. In some embodiments thereof, the curve in the distal end portion is between 10 and 45 degrees. In some embodiments, the cannulae are made of flexible materials, while in others each cannula has a geometry that imparts flexibility. Because the shaver typically has a much smaller cross-section than the typical lateral cage implant, it is expected that the areal-cross section of the bore of the inner cannula will be much smaller than the areal cross-section of the bore of the outer cannula. For example, in some embodiments, the bores of the cannulae each have an areal cross section, wherein the areal cross section of the bore of the inner cannula is less than 50% of the areal cross section of the bore of the outer cannula. More preferably, the areal cross section of the bore of the inner cannula is less than 25% of the areal cross section of the bore of the outer cannula. Preferably, the inner cannula is modular in order to customize for various angles of approach and inner geometry to guide various instruments. Thus, in some such embodiments, the inner cannula comprises upper 37 and lower 39 inserts having opposing faces 38,40. Preferably, the opposing faces each comprise a longitudinal groove 45,46 therein. These opposing grooves may help form the bore through which the shaver passes. Therefore, these grooves dictate the orientation of the shaver passing therethrough. Preferably, the lower insert is disposed only in a curved distal end portion of the port. This allows for easier access to the disc space in the portion of the port in which shaver head orientation is not critical.

In one particular embodiment thereof, the port comprises an outer cannula having a bore, and an inner cannula (disposed within the bore of the outer cannula) having internal guiding features. In these embodiments, these internal guiding features (such as grooves 45,46 and ridges) only allow the shaver is to be inserted into the disc space in such an orientation that the cutting surface of the shaver is parallel to the disc space.

The port can have variable distal angulations β within its distal end portion to ensure "snug" docking and control shaver angulations. The internal geometry of inserted or assembled port directs shaver into the disc space and maintains the axis of rotation.

Still referring to FIG. 6a-c, in some embodiments, there is provided a port for use in preparing an intervertebral disc space, which comprises a longitudinal bore 51 therethrough, the bore having a proximal end portion 53 having a transverse cross-section and a distal end portion 55 having a transverse cross-section, wherein the transverse cross-section of the proximal end portion of the bore is greater than that transverse cross-section of the distal end portion of the bore. The requirement that the transverse cross-section of the proximal end portion of the bore is greater than that transverse cross-section of the distal end portion of the bore provides the surgeon with greater room in the proximal section of the bore to maneuver the instruments, while insuring that the instrument is still properly oriented by the time it passes through the distal end of the port.

Preferably, the port having the larger proximal bore has a distal end portion that is curved in order to insure proper orientation of the instruments passing therethrough. Preferably, the curve in the distal end portion is between 10 and 45 degrees.

In some embodiments, the transverse cross-section of the proximal end portion of the bore is defined by an upper insert, and the transverse cross-section of the distal end portion of the bore is defined by a lower insert and an upper insert. These embodiments possess larger proximal bores whose advantages are discussed above. The inserts may be tailored to specifically and particularly accommodate and orient the different instruments that enter the port.

Thus, now referring to FIGS. 6a-c and 7a-c, in some embodiments, there is provided a port for use in preparing an intervertebral disc space, comprising:
a) an outer cannula 34 having a bore 36 having a proximal end portion 65 and a distal end portion 67,
b) an upper insert 37 disposed at least in the distal end portion of the bore, and
c) a lower insert 35 disposed at least in the distal end portion of the bore.

Preferably, the lower insert is disposed only in the distal end portion of the bore. Its absence in the proximal portion provides room for the surgeon to maneuver the shaver in the proximal portion of the port. Preferably, the upper insert is disposed in both the proximal and distal end portions of the bore. This is advantageous because it improves the ease and insertion along the entire length and provides the superior internal geometry to control insertion angle and axis of rotation. Preferably, the proximal end portion of the bore is straight, and the distal end portion of the bore is curved. The straight proximal end portion of the bore allows for accurate placement of the distal end portion of the port near the target disc space. Preferably, the distal end portion of the upper insert has a face 38, and the lower insert has a face 40, and the faces oppose each other, thereby forming a bore therebetween that dictates the orientation of the shaver passing therethrough.

Thus, and now referring to FIG. 7 a-c, there is provided an assembly comprising:
a) a curved port 91 having a bore having a transverse cross-section; and
b) a vertebral endplate shaver 95 having a transverse cross-section,
wherein the shaver is disposed within the bore of the curved port,
wherein the transverse cross-section of the bore substantially corresponds to the transverse cross-section of the shaver so as to determine the orientation of the shaver within the bore.

In some embodiments, the curved port has a distal end portion 33 having a securement feature 35 for securing the curved port to vertebral bone adjacent the target disc space. Preferably, the shaver is bendable so that it can pass through the curved portion of the port. In some embodiments thereof, the bendable shaver has a shaft 96 made of a flexible material, while in others the bendable shaver has a shaft having a universal joint.

In one prophetic method of practicing the present invention, the curved port enters the patient through an incision made in the skin. It then proceeds towards the target disc by manual advancement. Once in the general area of the target disc, the distal portion 33 of the port is then bent by advancing it over a steerable catheter that has itself been bent (as explained below). This leaves the distal end portion of the port adjacent the target disc. The securement tooth is advanced into a neighboring vertebral body to stabilize port placement. After the disc space is cleared, the flexible shaver is then advanced through the curved port and into the disc space. The inner features of the curved port guide the shaver's angulation with respect to the disc space. Once the shaver has been suitably placed, the handle and drive shaft of the shaver are rotated to scrape disc tissue and endplates in a plane that is parallel to the disc space.

Figure 7D:
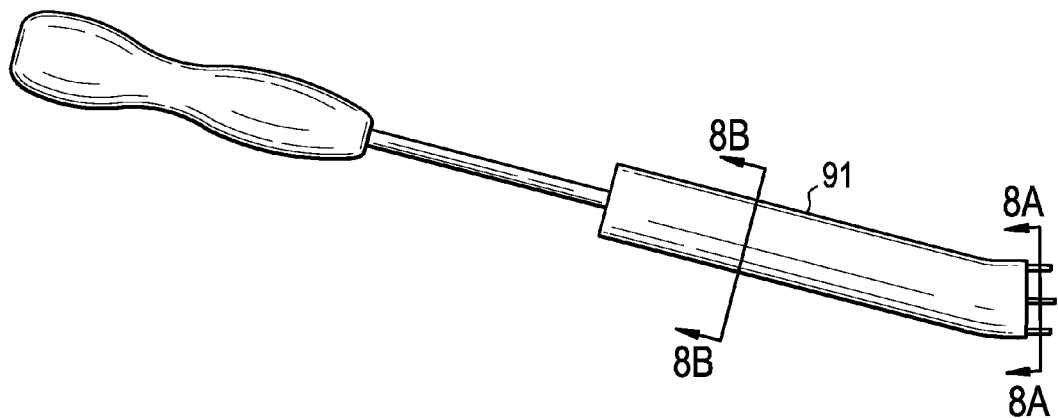
FIG. 7d discloses a handled port of the present invention.
Figure 8A:
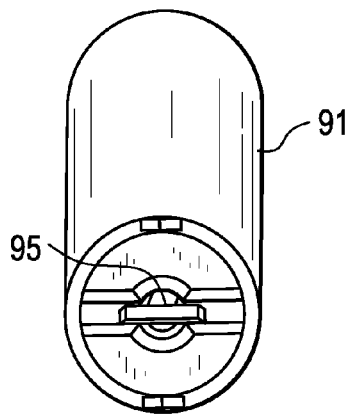
FIGS. 8a-b disclose cross-sectional views of the port of FIG. 7d.
Figure 8B:
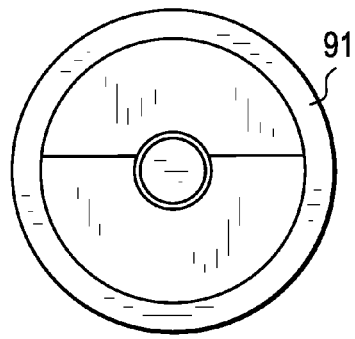

Therefore, in some embodiments, there is provided a method of preparing an intervertebral disc space between opposing vertebral endplates, comprising the steps of:
a) inserting a curved port into a lateral aspect of the disc space, the curved port having a bore.
FIG. 7d discloses a port 91 and shaver 95 of the present invention.
FIGS. 8a-b disclose cross-sectional views of the port-shaver assembly of FIG. 7d.

Preferably, the insertion is in a substantially coronal plane, as is generally the case for lateral implants. Preferably, the curved port has a substantially straight proximal end portion and a curved distal end portion. Preferably, the curved distal end portion of the curved port is docked to a vertebral body and is oriented substantially parallel to the opposing vertebral endplates in order to dictate endplate preparation that is parallel to the endplates. Preferably, the curved port has a distal end portion having a securement feature, through which docking of the port to a vertebral body occurs. This provides secure attachment of the port to a neighboring vertebral body.

In other embodiments, the method further comprises the steps of:
b) inserting a substantially straight, bendable shaver into the curved port;
c) advancing the shaver through the port and into an intervertebral disc space bounded by a vertebral endplate so that the shaver bends in the port, and
d) contacting the shaver to the vertebral endplate.

Preferably, the bore of the port has a shape corresponding to a cross-section of the shaver so as to determine the orientation of the shaver within the bore. Preferably, the bendable shaver has a shaft made of a flexible material, or has a shaft having a universal joint. Preferably, the target disc space is the L5/S1 or L4/L5 disc space. It is currently very problematic to access these two disc spaces with conventional lateral cage insertion techniques. Preferably, the curved port approaches the disc space during insertion from an upper end of the spine, as is the case with conventional lateral cage insertion techniques.

Now referring to FIGS. 9a-c, a catheter 101 with a steerable tip 103 is used to laterally access the caudal disc space. It is typically advanced through an incision in the skin of the patient and directed in a straight line towards the target disc. The steering mechanism in the catheter is then actuated to impart a curve in the tip of the catheter. This curve allows the surgeon to steer the tip directly towards the disc. The tip is then advanced until it contacts the target disc.

In some embodiments, a distal end portion 105 of the catheter includes a neuromonitoring sensor or electrode 141. This sensor connects to an external neuro-monitor as the catheter is advanced into the abdomen under fluoroscopic imaging. The function of this sensor is to detect the presence of nerves as the catheter tip is directed towards the target disc.

Once the tip is safely placed against a lateral portion of a disc, a guide wire 139 is advanced through the steerable tip and into the disc. In some embodiments, the electrode 141 can be a neuromonitoring band for sensing adjacent neural tissue. The function of this guide wire is to anchor the initial catheter in the disc and set the trajectory for the subsequent advance of dilation tubes.

In some embodiments, the steerable catheter and guidewire system is the VASCOCATH™, available from Polydiagnost of Pfaffenhofen, Germany.

Figure 10C:
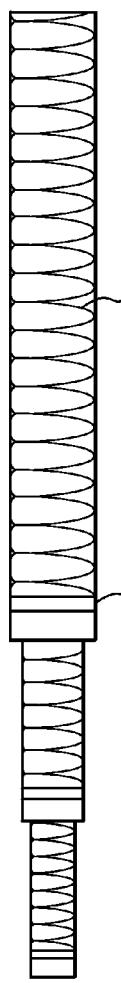
FIGS. 10c-e disclose telescoping dilation tubes.

Now referring to FIGS. 10a-c, the flexible dilation tubes 111,113,115 provide a minimally invasive access path for the subsequent advance of instruments or implants. Sequential flexible dilation tubes are advanced over the steerable catheter 101 and against the disc, thereby sequentially removing more and more tissue from the access path.

The flexible nature of these dilation tubes allows them to curve and thereby provide a parallel trajectory for instruments and implants laterally approaching the L4/L5 or L5/S1 disc spaces.

Therefore, and now referring to FIGS. 10a-c, in accordance with the present invention, there is provided an assembly for providing access to an intervertebral disc, comprising;
a) a catheter 101 having a steerable tip 103,
b) a first flexible dilator tube 111 having a first bore 112 defining a first longitudinal axis,
c) a second flexible dilator tube 113 having a second bore 114 defining a second longitudinal axis,
wherein the first flexible dilator tube is received with the bore of the second flexible dilator tube, and
wherein the steerable tip is received within the bore of the first flexible dilator tube.

Preferably, the steerable tip is curved, thereby imparting a curve upon the longitudinal axis of each of the first and second flexible dilator tubes. Preferably, each of the first and second dilator tubes has a proximal end portion and a distal end portion, and wherein the curve upon the longitudinal axis of each of the first and second flexible dilator tubes is located in the distal end portion of each tube.

In some embodiments, the catheter further comprises a guide wire.

In some embodiments, and now referring to FIGS. 10a-b, at least one of the flexible dilation tubes comprises a reinforcement member 131, preferably a fiber which is preferably metallic.

In some embodiments, each of the first and second flexible dilator tubes has a frustoconical distal end.

In accordance with the present invention, there is provided an assembly for providing access to an intervertebral disc, comprising;
d) a catheter having a steerable tip,
e) a first flexible dilator tube having a first bore defining a first longitudinal axis,
f) a second flexible dilator tube having a second bore defining a second longitudinal axis,
wherein the first flexible dilator tube is received with the bore of the second flexible dilator tube, and
wherein the steerable tip is received within the bore of the first flexible dilator tube.

In accordance with the present invention, there is provided a method of accessing a target intervertebral disc, comprising the steps of:
a) advancing a steerable catheter having a tip through an incision and towards the target disc,
b) imparting a first curve in the tip of the steerable catheter,
c) docking the curved tip upon the target disc,
d) advancing a first flexible dilator tube over the curved tip to impart a first curve in the first flexible dilator tube.

Figure 10D:
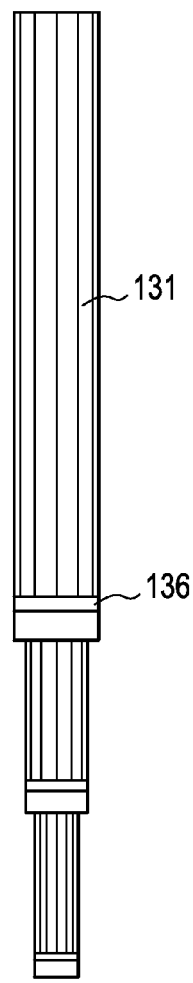
Figure 10E:
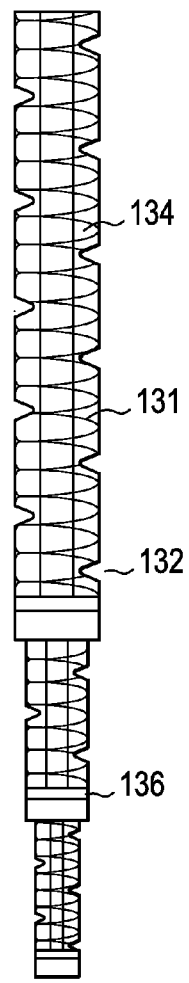

FIGS. 10c-e disclose telescoping dilation tubes. In FIG. 10c, each tube has helical reinforcement members 131 that are electrically connected to a neuromonitoring band 136. Thus, the ports may be used for neuromonitoring during approach. In FIG. 10d, each tube has vertical reinforcement members 131 that are electrically connected to a neuromonitoring band 136. In FIG. 10 e, each tube has helical and vertical members 131 that are electrically connected to a neuromonitoring band 136. It also has slots 132 that provide additional flexibility.

Figure 11:
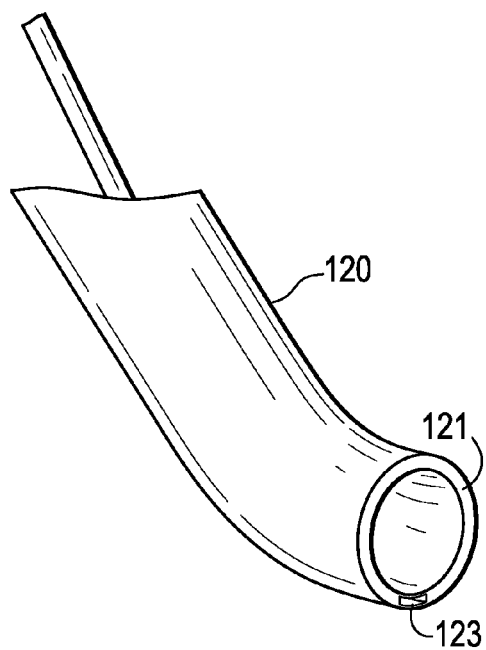
FIG. 11 discloses a flexible dilation tube with a bore for holding an endoscopic instrument.

Now referring to FIG. 11, the flexible dilation tubes comprise elastically deformable materials includes metallics and polymers. The flexible dilation tubes may further comprise axial reinforcing members (such as wires, fibers or struts) in order to provide improved column strength. The wall 121 of the flexible dilation tube 120 can have a secondary bore 123 to accept an endoscope for visualization of the disc and adjacent structures. Once dilation to the desired diameter is accomplished, the smaller dilation tubes may be removed. Inserts may be placed within the final dilation (or "port") in order to provide internal guiding surfaces for guiding instruments such as flexible shavers.

We claim:
1. A method of intervertebral disc space preparation, comprising the steps of:
a) selecting a shaver having a flexible shaft and a shaving head;
b) inserting the shaver into an intervertebral disc space bounded by opposed vertebral endplates, and
c) contacting the shaver to a vertebral endplate
d) shaving the vertebral endplate with the shaving head of the shaver by rotating the shaving head with the shaving head being substantially parallel to the vertebral end- plate and the flexible shaft being not substantially parallel to the vertebral endplate.

2. The method of claim 1 wherein the flexible shaft is made of a flexible material.

3. The method of claim 1 wherein the flexible shaft has a universal joint.

4. The method of claim 1 wherein the flexible shaft is slotted to impart flexibility.

5. The method of claim 1 wherein the flexible shaft comprises a spring.

6. A method of preparing an intervertebral disc space between opposing vertebral endplates, comprising the steps of:
 a) inserting a curved port into a lateral aspect of the disc space, the curved port having a bore.

7. The method of claim 6 wherein the insertion is in a substantially coronal plane of a human spine.

8. The method of claim 7 wherein the curved port has a substantially straight proximal end portion and a curved distal end portion.

9. The method of claim 8 wherein the curved distal end portion of the curved port is docked to a vertebral body and is oriented substantially parallel to the opposing vertebral endplates.

10. The method of claim 6 wherein the curved port has a distal end portion having a securement feature, and further comprising the step of:
 b) docking the port to a vertebral body via the securement feature.

11. The method of claim 6 further comprising the step of:
 b) inserting a substantially straight, bendable shaver into the curved port;
 c) advancing the shaver through the port and into an intervertebral disc space bounded by a vertebral endplate so that the shaver bends in the port, and
 d) contacting the shaver to the vertebral endplate.

12. The method of claim 11 wherein the bore of the port has a shape corresponding to a cross-section of the shaver so as to determine the orientation of the shaver within the bore.

13. The method of claim 11 wherein the bendable shaver has a shaft made of a flexible material.

14. The method of claim 11 wherein the bendable shaver has a shaft having a universal joint.

15. The method of claim 11 wherein the disc space is the L5/S1 disc space.

16. The method of claim 11 wherein the disc space is the L4/L5 disc space.

17. The method of claim 1 wherein shaving the vertebral endplate with the shaving head further comprises shaving the vertebral endplate with the entire flexed portion of the flexible shaft located outside of the intervertebral disc space.

18. The method of claim 6 wherein the curved port further comprises:
 an outer cannula having a bore, and
 an inner cannula having a bore, and
 wherein the method further comprises:
 b) inserting a substantially straight, bendable shaver into the inner cannula of the curved port.

19. The method of claim 18 wherein the inner cannula has a bore having a non-circular transverse cross-section.

20. The method of claim 18 wherein the bores of the cannulae each has an areal cross-section, wherein the areal cross-section of the bore of the inner cannula is less than 50% of the areal cross-section of the bore of the outer cannula.

21. The method of claim 20 wherein the inner cannula comprises upper and lower inserts having opposing faces and wherein the opposing faces each comprise a longitudinal groove therein.

22. The method of claim 11 further comprising:
 shaving the vertebral endplate with a shaving head of the shaver; and
 rotating the flexible shaft and rotating the shaving head while shaving the vertebral endplate and flexing the flexible shaft with the shaving head substantially parallel to the vertebral endplate.

* * * * *